United States Patent
Savin et al.

(10) Patent No.: US 8,624,582 B2
(45) Date of Patent: Jan. 7, 2014

(54) MEASURING METHOD, ARRANGEMENT AND SOFTWARE PRODUCT

(75) Inventors: Hele Savin, Espoo (FI); Antti Haarahiltunen, Perttula (FI); Marko Veli Yli-Koski, Espoo (FI)

(73) Assignee: Teknillinen Korkeakoulu, TKK (FI)

( * ) Notice: Subject to any disclaimer, the term of this patent is extended or adjusted under 35 U.S.C. 154(b) by 1492 days.

(21) Appl. No.: 12/083,091

(22) PCT Filed: Oct. 6, 2006

(86) PCT No.: PCT/FI2006/000327
§ 371 (c)(1),
(2), (4) Date: Sep. 4, 2008

(87) PCT Pub. No.: WO2007/042606
PCT Pub. Date: Apr. 19, 2007

(65) Prior Publication Data
US 2009/0160431 A1    Jun. 25, 2009

(30) Foreign Application Priority Data
Oct. 7, 2005    (FI) .................................... 20051009

(51) Int. Cl.
*G01R 23/20*    (2006.01)
*G01R 19/00*    (2006.01)

(52) U.S. Cl.
USPC .................... 324/128; 324/76.11; 324/140 R

(58) Field of Classification Search
None
See application file for complete search history.

(56) References Cited

U.S. PATENT DOCUMENTS

| 6,146,135 A * | 11/2000 | Watanabe et al. ............. 432/221 |
| 6,150,175 A | 11/2000 | Shelton et al. |
| 6,607,927 B2 | 8/2003 | Ramappa et al. |
| 2003/0064533 A1 | 4/2003 | Ramappa et al. |

FOREIGN PATENT DOCUMENTS

| JP | 01-278037 | 11/1989 |
| JP | 05-315428 | 11/1993 |
| JP | 2005-142359 | 6/2005 |

OTHER PUBLICATIONS

H. Vainola, et al., "Quantitative Copper Measurement in Oxidized p-type Silicon Wafers Using Microwave Photoconductivity Decay", Applied Physics Letters ,vol. 87, paper 032109, Jul. 15, 2005, pp. 1-3.
H. Vainola, et al., "Sensitive Copper Detection in P-type CZ Silicon Using uPCD", Journal of the Electrochemical Society, vol. 150 (12), Oct. 23, 2003, pp. G790-G794.

(Continued)

*Primary Examiner* — Jermele M Hollington
*Assistant Examiner* — Trung Nguyen
(74) *Attorney, Agent, or Firm* — Birch, Stewart, Kolasch & Birch, LLP

(57) ABSTRACT

The invention presents a method for determining the copper concentration of the substrate using the photoconductivity method in a new manner, the method comprising steps in which the photoconductivity property of the substrate is measured for a first time by an arrangement, the surface of the substrate is illuminated by illuminating means emitting photon radiation, the photoconductivity property of the substrate is measured for a second time by an arrangement, and the copper concentration of the substrate is determined from the change between the first and second time of measurement on the basis of the illumination. The invention also presents an arrangement and a software product for determining the copper concentration.

39 Claims, 1 Drawing Sheet

(56) References Cited

OTHER PUBLICATIONS

Figure 1:
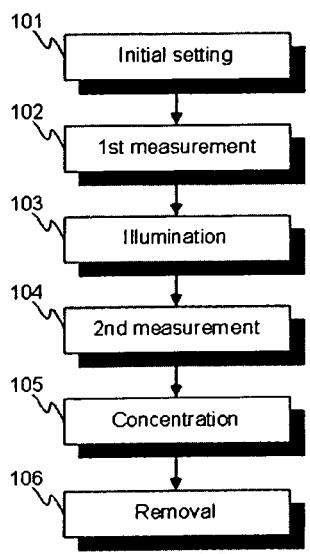
Figure 1:
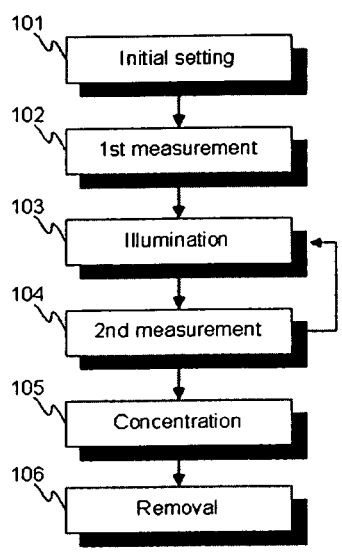

International Preliminary Report on Patentability for PCT/FI2006/000327 dated Apr. 9, 2008.
International Search Report for PCT/FI2006/000327 dated Jan. 29, 2007.
M. Yli-Koski, "Optical Activation of Copper in Silicon Studied by Carrier Lifetime Measurements", Dissertation for the degree of Doctor of Science in Technology, Helsinki University of Technology (Espoo, Finland), Nov. 12, 2004.
M. Yli-Koski, et al., "Detection of Low-Level Copper Contamination in p-type Silicon by Means of Microwave Photoconductive Decay Measurements", Journal of Physics: Condensed Matter, vol. 14, Nov. 22, 2002, pp. 13119-13125.
Written Opinion of the International Searching Authority for PCT/FI2006/000327 dated Jan. 11, 2007.

* cited by examiner

MEASURING METHOD, ARRANGEMENT AND SOFTWARE PRODUCT

In general, the invention relates to a photoconductivity measurement technique. In more particular, the invention relates to determining the concentration of copper impurities in a substrate in a manner stated in the preamble of the independent claim concerning the method. The invention also relates to an arrangement for determining the concentration of copper impurities in a substrate in a manner stated in the preamble of the independent claim concerning the arrangement. The invention also relates to a software product for determining the concentration of copper impurities in a substrate in a manner stated in the preamble of the independent claim concerning the software product.

Especially copper contamination is considered a problem in the branch of industry which manufactures IC circuits and photoelectric components. The problems are manifested as yield losses especially in the IC industry, whereas in photoelectric applications, such as solar cells, the reduction of the lifetime of cells caused by copper deteriorates their efficiency. In particular, it has been difficult to detect even a local, low copper contamination in a silicon wafer of the p-type and to measure a potential contamination on a quantitative level in a non-contacting manner.

There have been attempts to alleviate the problem entailed by the contamination concentrations by a technique, which is known as such. A prior art reference is in the dissertation Optical Activation of Copper in Silicon Studied by Carrier Lifetime Measurements (ISBN 951-22-7233-4) [1] by Marko Yli-Koski, 2004, in which some aspects associated with the subject have been dealt with. According to the dissertation, optical activation of copper takes place in circumstances where there is a large number of excess charge carriers when the boron-doped silicon contains interstitial copper atoms. Because of their positive charge, it is possible to use a positive corona charge to prevent the diffusion of interstitial copper from p-type bulk silicon to the silicon surfaces. When positive charge is used on the silicon surfaces, it has been proved that interstitial copper is found for a long time from boron-doped bulk silicon during storage. In addition, it is mentioned that the recombination activity caused by the activation of copper after a long optical illuminating time is independent of the light intensity. A well-known prior art method is to carry out the optical activation in a spot-like manner using infra-red laser light (973.5 nm) with an intensity higher than 25 W/cm$^2$.

According to the prior art, low copper contamination has not been found to have an effect on the lifetime of charge carriers in p-type silicon. In order to detect copper contamination in an indirect manner, n-type wafers have been used as monitoring wafers beside the p-type wafers, because the lifetime reaction to copper is stronger in the n-type. With this method, there is no certainty as to whether the reduction of lifetime detected in the n-type is caused by copper or other contaminants.

A known method is also to measure copper from p-type silicon by the SPV method, (Surface PhotoVoltage), which measures the diffusion length (U.S. Pat. No. 6,607,927) [2] of the charge carriers. Here the measurement takes place in a weak injection. The wafer to be measured is illuminated by a light source having a minimum power of 2.5 W/cm$^2$ or heated for 15 minutes at 300° C. The effect of light reduces the diffusion length. Both copper and iron cause a reduction of the diffusion length. A drawback in the method is the long waiting time after heating or illuminating, which is relatively long with respect to the actual heating, during which waiting time iron and boron are able to form Fe-B pairs. Only after that it is possible to determine the copper concentration from the diffusion length according to the description in [2]. A drawback of the method is the diffusion of copper directed to the surface, wherein the part of copper which has reached the surface is not taken into account or not detected at all, because the copper ions diffused on the surface do not have an effect on the diffusion length of the charge carriers as such.

It is an object of the invention to solve the prior art problems or at least to alleviate their effect. It is also an object of the invention to provide a method for detecting the lateral distribution of copper in a substrate. Another object of the invention is to provide a device for detecting the lateral distribution of copper in a substrate. Yet another object of the invention is to provide a software product for detecting the lateral distribution of copper in a substrate and for presenting it graphically.

The object of the invention is achieved by determining the copper concentration from the change in the photoconductivity property by photoconductivity measurements before and after an illuminating period in which the substrate is illuminated for the whole surface area to be measured.

The method according to the invention is characterized in what is set forth in the characterizing part of the independent claim concerning the method.

The arrangement according to the invention is characterized in what is set forth in the characterizing part of the independent claim concerning the arrangement.

The software product according to the invention is characterized in what is set forth in the characterizing part of the independent claim concerning the software product.

Other embodiments of the invention are presented in the subclaims. The embodiments of the invention can be combined with each other for the applicable parts, if not expressly stated otherwise.

In this document, the photoconductivity property means the changing of photoconductivity caused by excess charge carriers, especially its reduction, in proportion to time because of the recombination of charge carriers, but also the recombination speed of the excess charge carriers in an equilibrium.

In this document, non-contacting measurement means that in the actual measuring situation, the non-contacting measuring device does not couple the substrate to be measured by a galvanic coupling, for example, as part of a closed electrical circuit with the measuring device during the performance of the measurement. In addition, the non-contacting method maintains the material to be measured essentially undestroyed during the measurement, with the exception of harmful constituents possibly removed from the material to be measured.

In this document, illumination means directing a certain photon radiation of a light source selected for the purpose, having a certain distribution of wavelengths, for a predetermined period of time on the surface of the substrate to be measured, with the purpose of activating copper in such a way that the recombination of charge carriers associated with it is strengthened. This strengthened recombination can be measured by the photoconductivity property measurement.

The relatively long response time of copper to react to illumination is utilized in the embodiments of the invention. For measuring the copper concentration, an insulation layer, e.g. a layer of oxygen or nitride, is grown on a substrate, such as a silicon wafer of the p-type when required, according to the purpose of use, which insulation layer efficiently prevents the access of copper ions from the inside of the sample to the surface of the sample during cooling and in room temperature. The growing can be performed thermally, but also chemically as an alternative, for the applicable parts. The substrate can also be a so-called native wafer, in which case a layer of oxide or some other insulator need not be grown on it, because such a layer of a certain thickness is naturally formed on it. In that case, an in-situ corona charge must be used when measuring the wafer. When the charge is used, the sample need not be quenched or the sample stored below room temperature between heating and measurement. When the insulation layer has been formed, a charge is created on top of the insulation layer of substrate, e.g. in a non-contacting manner by means of a corona charger causing an electric field on the surface of the substrate, which prevents the access of positive copper ions/atoms to the surface of the sample during the illumination to be carried out later.

In a method according to an embodiment of the invention, a method known as such for determining the photoconductivity property, e.g. the μPCD-method (microwave photoconductive decay), or some other method, for measuring the photoconductivity property of the sample is used. According to an embodiment of the invention, a high excess charge carrier concentration (large injection) is used in the photoconductivity property measurement, but in another embodiment of the invention, the excess charge carrier concentration is small (weak injection). In another embodiment of the invention, the excess charge carrier concentration is between a large and a weak injection, when the largeness and smallness of the injection is estimated in a framework understood by a person skilled in the art. In a method according to an embodiment of the invention, the photoconductivity property measurement is carried out in a non-contacting manner, in which case the advantage is that the substrate is not destroyed, but the invention is not to be limited to non-contacting photoconductivity measurement methods only.

According to an embodiment of the invention, there are at least two measurements, between which the sample is illuminated essentially for its whole surface, which is the object of the examination. According to an embodiment of the invention, the illumination can also be focused on a part of the surface of the substrate to be examined. According to an embodiment of the invention, said part is a macroscopic, not spot-like area, from which the lateral distribution of copper can be determined. During the illumination, the copper ions precipitate and the iron-boron pairs break up. The formation of copper precipitates is seen as the shortening of the lifetime of the charge carriers. The breaking up of the iron-boron pairs is seen in the measurements as an increase of the lifetime of the charge carriers. Copper contamination can then be distinguished from iron contamination quickly, even in less than a few tens of minutes with regard to qualitative determination, because the change of lifetime has an opposite direction and is slow in copper as compared to iron. In that case, the method according to the embodiment of the invention provides an advantage over the SPV method, for example, because in SPV both the formation of copper complexes and the breaking up of the iron-boron pairs cause shortening of the lifetime of the charge carriers. Obtaining the difference between the factors causing the contamination may even take many days, and SPV is thus not very suitable for increasing the efficiency of the process, especially with regard to the control of the feedback. According to an alternative embodiment of the invention, the copper concentration and/or the lateral distribution of copper in the substrate can be determined quantitatively, in which case the total duration of the illumination can be many hours, especially with very low copper concentrations, in which case, however, the copper distribution of the whole substrate is achieved with one period of total illumination, when required.

In the embodiments of the invention, areas having a diameter clearly smaller than 1 mm are regarded as spot-like.

When the photoconductivity property measurement, from which the lifetime of the excess charge carriers is found out, is carried out twice according to the embodiment of the invention, before and after the illumination, the copper concentration is found out from the change of the lifetime of the excess charge carriers, which in the case of copper is shortening between measurements. The photoconductivity property measurement can preferably be carried out by a scanning device, which is advantageously according to the embodiment of the invention a non-contacting device. When it is also taken into account that the crystal defects caused by the oxygen precipitates of the silicon wafer also have an effect on the lifetime of the charge carriers caused by the copper precipitates, the sensitivity of detection can be increased by taking the oxygen precipitates into account. The concentration of the oxygen precipitates can be measured separately and/or determined on the basis of the history of manufacture of the substrate.

In the method according to the embodiment of the invention, it is also possible to use an electric field to eliminate the out-diffusion of copper, and measurement need not necessarily be performed immediately after processing. The electric field required can also be formed on the surface of the substrate for eliminating the out-diffusion of copper by other means alternative to the corona charger.

As an advantage of the embodiments of the invention it may be mentioned that the illumination power can be kept relatively low, which provides a considerable advantage, because the purchase price and operating costs of the light source remain low. In addition, because in the embodiments of the invention, illumination is focused on the whole surface of the substrate to be examined, it is clearly faster to create impurity maps than in methods using spot-like illumination, and the lateral resolution gained by the map can be even in a millimetric scale. In addition, because in the illumination according to the embodiment of the invention, the lifetime change caused by copper is in the opposite direction to that caused by iron, it is possible to detect immediately, i.e. in about 10 minutes, in a qualitative manner, whether there is copper, iron, neither or both in the substrate.

By using a long illumination time also with low copper concentrations according to an embodiment of the invention, the copper concentration can be determined in a quantitative manner and present the lateral distribution of copper on the substrate graphically.

Because the same substrate can be measured many times without destroying the substrate when measuring by a non-contacting method, the same substrate can also be used for localizing the source of copper contamination in the process.

Figure 2:
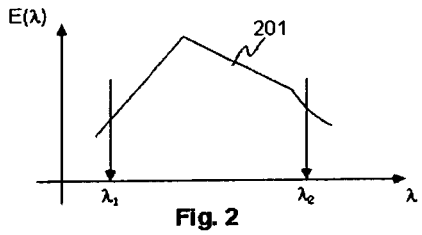
Figure 4:
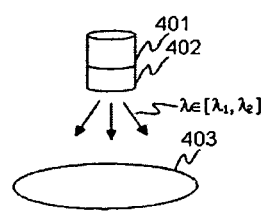
Figure 3:
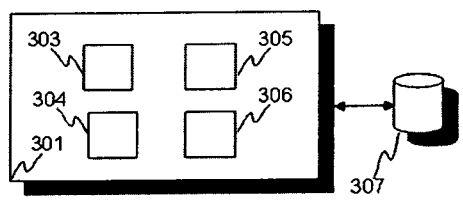

In the following, the embodiments of the invention will be described in more detail with reference to the following drawings, in which FIG. 1A illustrates a method according to an embodiment of the invention, FIG. 1B illustrates a method according to another embodiment of the invention, FIG. 2 illustrates the wavelength distribution used in the illumination according to an embodiment of the invention, FIG. 3 illustrates an arrangement according to an embodiment of the invention, and FIG. 4 illustrates the illumination step according to an embodiment of the invention, FIG. 1A illustrates the non-contacting method according to an embodiment of the invention for determining the copper concentration of the substrate by a photoconductivity property measurement. The non-contacting method provides the advantage that the substrate being measured is not unnecessarily destroyed, but for saving material costs, it can be used for the original purpose of use for which the substrate was manufactured. The method comprises steps in which the photoconductivity property of the substrate is measured for a first time 102, e.g. by an arrangement having μPCD equipment or corresponding parts, and after the measurement the surface of the substrate is illuminated 103 by illuminating means emitting photon radiation, and the photoconductivity property is measured 104 for a second time. In step 105, the copper concentration of the substrate is determined from the change between the first 102 and the second 104 time of measurement on the basis of the illumination 103.

FIG. 1B shows an embodiment variant of the invention in which a series of second measurements 104 is performed on the basis of the progress of the illumination during the total duration of the illumination 103, which is illustrated by an arrow from step 104 back to step 103. Then the illumination can be performed as continuous and the photoconductivity property 104 be measured at certain measurement intervals. Illumination can also be performed periodically, so that during a certain part of the period, the first subperiod, the surface of the substrate is illuminated by photon radiation for a period of time having the duration of a certain first period of time, and not illuminated during a certain second subperiod having the duration of a certain second period of time, which has the length of the period with the first subperiod excluded. According to an embodiment of the invention, the periods can be repeated for achieving a certain total period of illumination.

The time between the measurements 104 can be kept essentially constant in an embodiment of the invention, but without being limited to repeated measurements at constant intervals only. According to yet another embodiment variant of the invention, illumination is performed in parts so that according to an embodiment, the measurement 104 can be carried out at certain predetermined points between the parts of illumination, but can alternatively also be carried out after each partial illumination. According to an embodiment variant of the invention, the durations of the partial illuminations can be of different lengths, and according to yet another embodiment of the invention, partial illuminations can be performed with photon radiation of different wavelengths, having a different distribution of wavelengths in each partial radiation, but without being limited to said photon radiation only. According to an embodiment of the invention, the period of time between the illuminations is set in advance, but the periods need not necessarily be of the same length, but at least some of them may have a length different from the others. According to an embodiment of the invention, the time of illumination of the illumination periods, the duration of the first period of illumination, is selected logarithmically, in which case it is possible to determine on the basis of the results how qualitative or quantitative the copper concentration values are, but the measurement need not be separately stopped and/or started again.

In FIGS. 1A and 1B, the initial setting 101 illustrates the measures which are performed at first in the method, such as achieving an insulating layer and the use of corona or other electric field, but also the measures that a person skilled in the art knows to be performed for preparing the substrate for the measurement of the photoconductivity property. Then, for example, placing the substrate on the place of measurement and/or for illumination can be performed either manually and/or automatically. With automatic placement, it is possible to achieve a measurement cycle suitable for serial production, in which a first substrate is in measurement 102, a second one in illumination 103 and a third one in the second measurement 104, in which case the places of illumination and measurement 103, 104 are not necessarily all the same. According to another automated embodiment of the invention, the places of measurement and illumination are the same, in which case the same substrate is handled through the cycles 102, 103, 104, 105 on the same place without moving the substrate between the steps. In step 106, the substrate is removed from the measurement, e.g. removed from the place of measurement, and the required presettings are set for a new measurement. Then the step of initial settings may include steps that overlap with the removal for the applicable parts in an embodiment of the invention.

According to an embodiment of the invention, the photon radiation used in the method has a distribution of wavelengths between a first and a second wavelength. This is illustrated in FIG. 2, in which the distribution curve is continuous. Said distribution is represented as energy as a function of the wavelength, in which case the photon flux can be estimated on each wavelength within the error limits. According to an embodiment of the invention, at least one of the mentioned first and second wavelength are in the wavelength range of visible light. The distribution curve 201 drawn in FIG. 2 is angular and thus bumpy, but the invention is not to be limited to a continuous distribution according to the figure only, but the distribution may be more rounded in shape. According to an embodiment of the invention, the distribution may also be discrete, in which case it may have many monochromatic or essentially monochromatic wavelengths. According to an embodiment of the invention, one of the wavelengths may also be coherent photon radiation.

According to a practical embodiment of the invention, the photon radiation used for illumination and generated by a light source in the method has a wavelength distribution 201, which comprises the wavelength distribution of a halogen lamp. According to another embodiment of the invention, the light source is a mercury lamp, but according to yet another embodiment of the invention, the light source may also contain filling gases or other substances, either in the lamp, the casing of the lamp and/or some other part of the lamp for processing the wavelength and/or intensity of the radiation emitted by the lamp. However, preferably according to an embodiment of the invention, the wavelength distribution of the radiation of the photons of the light source is essentially the distribution of ordinary daylight.

According to an embodiment of the invention, the duration of the illumination in the method depends on the copper concentration to be determined.

According to an embodiment of the invention, in an embodiment suitable for determining the lateral distribution of qualitative copper, the illumination time in its entirety, the total illumination time, is less than 30 minutes, preferably under 20 minutes and even more preferably under 15 minutes. According to an embodiment of the invention, the duration of the illumination is less than 10 minutes, but more than 5 minutes. According to an embodiment of the invention, the illumination is carried out by partial illuminations of less than 1 minute, preferably by partial illuminations of less than 3 minutes, but even more preferably by partial illuminations of less than 5 minutes. According to an embodiment of the invention, a short illumination time is selected with regard to qualitative determination.

According to another embodiment of the invention, for determining the quantitative, lateral distribution of copper, the illumination time can be as long as several hours, even 24 hours, if the copper concentration is known to be low, and oxygen precipitates, for example, are not expected to be present in the substrate, the copper concentration of which is determined. In that case, according to an embodiment of the invention, the illumination time in its entirety, the total illumination time, is less than 30 hours. According to an embodiment of the invention, it is less than 20 hours, but according to yet another embodiment, it is less than 15 hours. According to an embodiment of the invention, the duration of the illumination is less than 10 hours, but preferably generally more than 0.5 hours in a quantitative measurement. According to an embodiment of the invention, the illumination in a quantitative measurement is carried out by partial illuminations of less than an hour, preferably by partial illuminations of less than 3 hours, but even more preferably by partial illuminations of less than 5 hours. However, it is stated that with high copper concentrations and/or with substrates containing high oxygen precipitate concentrations, a quantitative measurement of copper concentration according to the embodiment of the invention can be carried out, depending on the concentration, even according to some embodiments according to the illumination times of qualitative measurement.

According to an embodiment of the invention, the total power of the illumination means used in the method on the substrate to be illuminated is lower than 1 W/cm$^2$. Preferably, the illumination is carried out in the method using a power in the range of 0.01 to 0.045 W/cm$^2$. According to an embodiment of the invention, the power is constant, but in other embodiments of the invention, it is not wanted to be limited to constant power only. According to an embodiment of the invention, the total power of the illumination is in the range of 0.15 to 0.4 W/cm$^2$.

According to an embodiment of the invention, the maximum illumination power is equal to 40 W/cm$^2$ or under 40 W/cm$^2$. According to another embodiment of the invention, the maximum illumination power is less than 4 W/cm$^2$. According to another embodiment of the invention, the maximum illumination power is less than 2 W/cm$^2$.

According to an embodiment of the invention, one illumination power of those mentioned is the illumination power of the light source. According to another embodiment of the invention, one illumination power of those mentioned is the illumination power on the part of the substrate being illuminated.

The method according to an embodiment of the invention can be used to handle a substrate, which contains silicon and/or is a silicon wafer. According to an embodiment of the invention, the wafer need not contain silicon as the main component; it may also be some other substrate, which is used for manufacturing a semiconductor.

FIG. 3 illustrates an arrangement 301, by which the determination of copper concentration according to an embodiment of the invention concerning the method can be carried out. However, FIG. 3 is not intended to limit the arrangement to the configuration shown in the drawing, but it may also contain a larger or smaller number of means. For example, the display or a corresponding graphical means has not been drawn in the figure inside the closed line, which depicts the arrangement 301 on a general level, neither a microprocessor or the read-alter storage needed by it, in which a mathematical model for determining the concentration on the basis of measurement information, for example, could be runnable or placed, or other required control means.

The arrangement 301 of FIG. 3 comprises illumination means 303 for performing the illumination, measuring means 304 suitable for photoconductivity measurement as arranged for performing the photoconductivity measurement before and after an illumination performed with illumination means. The illuminating means may also be of the type illustrated in FIG. 4, but without being limited to it in the embodiments of the invention. Depending on the total duration of the illumination, the measurement can be quantitative or qualitative. The measuring means 304 can be implemented as a scanner, for example, arranged for carrying out a microwave measurement, with regard to creating a graphical presentation of the copper distribution. In addition, the arrangement 301 includes means for determining 305 the copper concentration on the basis of the photoconductivity property measurement. Said means 305 may comprise physical means according to an embodiment of the invention, but said means 305 can also be, according to another embodiment of the invention, entirely or partly implemented by software means for the applicable parts. In addition, according to an embodiment of the invention, the arrangement 301 includes means 306 for removing the measured substrate from the place of the arrangement in which the illumination and/or measurement has been performed. These means 306 may also comprise the means required for performing and/or controlling an automatic measurement according to an embodiment of the invention. The means 305 and 306 may also be adapted to operate in an arrangement functioning according to the principles of serial production, in which case the illumination and the measurement itself can be phased according to an embodiment of the invention, i.e. the illuminating and the measurement are carried out on different wafers, but without being limited to phasing. According to an embodiment of the invention, the photoconductivity measurement has been arranged for a non-contacting measurement.

Embodiments, in which the illumination of the substrate is performed either entirely or partly in at least two different places, are not wanted to be excluded from the embodiments of the invention.

According to an embodiment of the invention, the arrangement 301 may also comprise means for feeding the substrate at the beginning of the measurement to the measurement area of the arrangement. With regard to embodiments for serial production, for example, these means have been adapted to function together with the removal means 306, but the feeding means may be included in the removal means for the applicable parts. In addition, in embodiments adapted for serial production and/or phased, the operation of the feeding and removal means between different phases may be arranged in such a manner that, for example, the means that function to remove the substrate from the first illumination also feed the substrate to the illumination. On the basis of the above exemplifying embodiment, a person skilled in the art can arrange the substrate feed and removal automation in many ways, but without departing from the scope of the invention according to the embodiment. However, according to an embodiment of the invention, the processing related to the measurement of the substrate can be controlled by software means, which can be placed either in connection with the arrangement or in connection with the means performing the automatic measurement operations related to the processing of the substrate itself.

According to an embodiment of the invention, the arrangement also includes memory and/or database means 307 for classifying and/or saving measurement data. Although the arrangement 301 is drawn within a closed line in FIG. 3, the way it is drawn is not intended to limit the arrangement into a mere device according to an embodiment of the invention, but said parts 303, 304, 305, 306 and/or 307 may also be separate where applicable, according to an embodiment of the invention in which at least one of said parts is separate from the rest of the arrangement.

FIG. 4 illustrates the illumination according to an embodiment of the invention for illuminating a surface of the whole substrate 403 by illuminating means that emit photon radiation at the wavelength λ, which is in the wavelength range according to FIG. 2. In practice, it is advantageous to illuminate only one side of the substrate at a time according to an embodiment of the invention. However, according to another embodiment of the invention, the substrate can be illuminated and/or measured on both sides simultaneously. In such an embodiment of the invention, a support is used on the substrate, the support being transparent with regard to the illumination and consisting of plastic or glass suitable for the purpose, and/or of a fluid bed as an alternative or in addition to that. The fluid can be some liquid, air or gas, which has a sufficient electric resistivity for performing the photoconductivity property measurement. The illuminating means 401, 402 are shown in the drawing, in which case 401 can be the light source itself equipped with means required for controlling it, and 402 the optical part of said illuminating means for focusing the illumination as arranged on the entire side of the substrate 403 to be illuminated at a time. If it is desired, according to an embodiment of the invention, to perform illumination on both sides of the substrate, either turning means for turning the substrate 403 have to be used or illuminating means be used on both sides of the substrate.

According to an embodiment of the invention, the arrangement also includes corona means for manipulating the distribution of the impurity copper in the depth direction. These means are preferably arranged to drive the copper ions to a certain part of the substrate, such as the surface. According to an alternative embodiment of the invention, the arrangement may also comprise electric field means instead of corona means for arranging an electric field on the substrate and thereby manipulating the distribution of the impurity copper in the depth direction.

An arrangement according to an embodiment of the invention includes display means for indicating the impurity copper concentration from a certain part of the substrate graphically, as a map, for example. These means can be implemented by program means, for example, for controlling the physical display on the basis of the concentration values either directly from the substrate to be measured or on the basis of values obtained from the database.

In an embodiment of the invention, the measurement of the photoconductivity property is performed with a measuring device, which is a scanning microwave scanner, or μPCD scanner, for example.

A software product according to an embodiment of the invention comprises means in computer-readable form for performing the method according to the embodiment of the invention. Then the software product may have control means as arranged for performing the photoconductivity property measurement, means for determining the lateral distribution of copper on the basis of the photoconductivity property measurements and/or database means for saving the measurement results for presentation. According to an embodiment of the invention, the software product also includes means for controlling the illumination, and preferably a user interface for changing and/or setting the settings and/or information of the software product.

In an embodiment of the invention, the copper concentration can be determined by means of a mathematical model by using the photoconductivity values and/or the change as a result of consecutive illuminations as the input data, on the basis of the values measured with the measuring device. Then the mathematical model may also comprise the function between the copper and the photoconductivity property in accordance with the dependency known as such. According to an embodiment of the invention, in this context it is also possible to use other methods than the μPCD method for determining the photoconductivity property.

The invention claimed is:

1. A method for determining a copper concentration of a substrate, the method comprising:
   measuring a photoconductivity property of the substrate for a first time;
   illuminating an area of the substrate on which the photoconductivity property is determined by photon radiation, the photon radiation having a wavelength distribution between a first and a second wavelength;
   measuring the photoconductivity property of the substrate for a second time; and
   determining a lateral distribution of the copper concentration of the illuminated area of the substrate from the change between results of the first and the second measurement.

2. A method according to claim 1, wherein the photon radiation used in the method has a wavelength distribution, which includes the wavelength distribution of a halogen lamp.

3. A method according to claim 1, wherein the wavelength distribution of the photon radiation used in the method includes a wavelength in which the photon radiation is coherent.

4. A method according to claim 1, wherein the duration of the illumination in the method depends on the copper concentration to be determined.

5. A method according to claim 4, wherein the duration of the illumination in the method also depends on the concentration and/or size of the oxygen precipitates.

6. A method according to claim 1, wherein, in the method, illumination is carried out sequentially in periods, so that during a certain part of the period, the first subperiod, the surface of the substrate is illuminated by photon radiation for a period of time having the duration of a certain first period of time, and not illuminated during a certain second subperiod having the duration of a certain second period of time.

7. A method according to claim 6, wherein the periods are repeated in the method.

8. A method according to claim 1, wherein the method is a non-contacting method.

9. A method according to claim 1, wherein the duration of the illumination in its entirety in the method is less than 30 minutes.

10. A method according to claim 1, wherein the duration of the illumination in its entirety in the method is less than 10 minutes.

11. A method according to claim 1, wherein the duration of the illumination in its entirety in the method is in the range of 15 to 30 minutes.

12. A method according to claim 1, wherein the duration of the illumination in its entirety in the method is in the range of 5 to 15 minutes.

13. A method according to claim 1, wherein the duration of the illumination in its entirety in the method is less than 30 hours.

14. A method according to claim 1, wherein the duration of the illumination in its entirety in the method is less than 10 hours.

15. A method according to claim 1, wherein the duration of the illumination in its entirety in the method is in the range of 5 to 20 hours.

16. A method according to claim 1, wherein the duration of the illumination in its entirety in the method is in the range of 0.5 to 15 hours.

17. A method according to claim 1, wherein the maximum light power is equal to 40 W/cm$^2$ or under 40 W/cm$^2$.

18. A method according to claim 1, wherein the maximum light power is under 4 W/cm$^2$.

19. A method according to claim 1, wherein the maximum light power is under 2 W/cm$^2$.

20. A method according to claim 1, wherein the illumination is carried out in the method with a total power of an illumination source of less than 1 W/cm$^2$.

21. A method according to claim 1, wherein the illumination is carried out in the method with a total power of an illumination source of less than 0.1 W/cm$^2$.

22. A method according to claim 1, wherein the illumination is carried out in the method with a total power of an illumination source in the range of 0.01 to 0.04 W/cm$^2$.

23. A method according to claim 1, wherein the illumination is carried out in the method with a total power in the range of 0.05 to 0.4 W/cm$^2$.

24. A method according to claim 1, wherein the illumination is carried out in the method with a total power in the range of 0.15 to 0.4 W/cm$^2$.

25. A method according to claim 1, wherein the substrate used in the method contains silicon as the main constituent or is a silicon wafer.

26. A method according to claim 1, wherein, in the method, a first photoconductivity property measurement is performed before illumination, and a second photoconductivity property measurement is performed after illumination, in which case the photoconductivity property measurement is a μPCD measurement.

27. A method according to claim 1, wherein the measurement results are arranged to a map of the copper concentration in the substrate.

28. An arrangement for determining a copper concentration of a substrate, the arrangement comprising:
  a measuring device for measuring a photoconductivity property of the substrate for a first time;
  an illumination source for illuminating by photon radiation having a wavelength distribution between a first and a second wavelength an area of the substrate on which the photoconductivity property is determined;
  a measuring device for measuring the photoconductivity property of the substrate for a second time; and
  a determination unit for determining a lateral distribution of the copper concentration of the illuminated area of the substrate from the change between results of the first and the second measurement.

29. An arrangement according to claim 28, the arrangement further including a feeding unit for feeding the substrate for the photoconductivity property measurement.

30. An arrangement according to claim 29, where said feeding unit is configured to be automated for serial production.

31. An arrangement according to claim 29, said arrangement further comprising a charging unit for charging the surface of the substrate in order to direct the impurity copper to a certain part of the substrate.

32. An arrangement according to claim 31, in which a mathematical model is used to determine the copper concentration from the substrate.

33. An arrangement according to claim 32, further comprising a graphical device for indicating the concentration of impurity copper from a certain part of the substrate as a concentration map.

34. An arrangement according to claim 28, where one measuring device performs the first and the second photoconductivity property measurements, and said one measuring device comprises a scanning measuring head.

35. A software product encoded in a non-transitory computer-readable medium for performing a method for determining a copper concentration of a substrate, the software product, when run in a computer, performing the method which comprises:
  measuring a photoconductivity property of the substrate for a first time;
  illuminating an area of the substrate on which the photoconductivity property is determined is illuminated by photon radiation, the photon radiation having a wavelength distribution between a first and a second wavelength;
  measuring the photoconductivity property of the substrate for a second time; and
  determining a lateral distribution of the copper concentration of the illuminated area of the substrate from the change between results of the first and the second measurement.

36. A software product according to claim 35, said software product containing executable instructions, wherein the instructions cause the computer to
  perform the photoconductivity property measurement,
  determine the lateral distribution of copper on the basis of the photoconductivity measurements, and/or
  save the measurement results in a database for presentation.

37. A software product according to claim 36, said software product further containing executable instructions which cause the computer to control the automatic substrate feeding.

38. A software product according to claim 36, said software product further containing executable instructions which cause the computer to show copper concentration maps on the basis of the photoconductivity measurements, on a display device.

39. A software product according to claim 36, said software product further containing executable instructions which cause the computer to include, in said determining step, the effect of the oxygen precipitates on the copper precipitation in the substrate.

* * * * *